United States Patent [19]
MacMorran

[11] Patent Number: 5,827,207
[45] Date of Patent: Oct. 27, 1998

[54] NIGHT SPLINT

[76] Inventor: Ian MacMorran, 2017 First Ave., San Diego, Calif. 92101

[21] Appl. No.: 509,491

[22] Filed: Jul. 31, 1995

[51] Int. Cl.$^6$ ..................................................... A61F 5/00
[52] U.S. Cl. ................................... 602/5; 602/20; 602/21; 602/62; 128/845; 128/846; 128/877; 128/878
[58] Field of Search .................................. 602/5, 6, 9, 20, 602/21, 23, 26, 60, 62, 61, 64; 128/877–879, 882, 846; 473/59, 60, 61, 62, 63

[56] References Cited

U.S. PATENT DOCUMENTS

| | | |
|---|---|---|
| D. 259,955 | 7/1981 | Helferich ............................. 602/21 X |
| 2,738,190 | 3/1956 | Tureaud ..................................... 473/59 |
| 3,344,436 | 10/1967 | Stubbs ....................................... 473/59 |
| 3,606,614 | 9/1971 | Dimitroff ................................... 473/59 |
| 3,788,307 | 1/1974 | Kistner . |
| 3,818,905 | 6/1974 | Lebold ...................................... 602/21 |
| 3,903,878 | 9/1975 | Spann ....................................... 602/21 |
| 4,425,913 | 1/1984 | Lewis ....................................... 128/877 |
| 4,492,225 | 1/1985 | Picolet et al. ............................... 602/5 |
| 4,807,606 | 2/1989 | Hasegawa . |
| 4,829,992 | 5/1989 | Cilladi . |
| 4,883,073 | 11/1989 | Aziz . |
| 4,996,979 | 3/1991 | Grim et al. .............................. 602/21 |
| 5,058,576 | 10/1991 | Grim . |
| 5,069,203 | 12/1991 | Anderson . |
| 5,277,954 | 1/1994 | Carpenter et al. ........................ 428/71 |
| 5,382,225 | 1/1995 | Sutcliffe ................................... 602/24 |
| 5,385,537 | 1/1995 | Davini ..................................... 602/21 |

FOREIGN PATENT DOCUMENTS 2156225   10/1985   United Kingdom ................... 128/878

OTHER PUBLICATIONS

Slater & Bynum, Diagnosis and Treatment of CTS, Oct. 1993.

*Primary Examiner*—Richard J. Apley
*Assistant Examiner*—Kim M. Lee
*Attorney, Agent, or Firm*—Arthur F. Holz

[57] ABSTRACT

A soft-sided splint for rest and therapy of a stressed joint is constructed of fabric and batting and stiffened by one or more battens running the length of the generally tubular shape of the splint. Specific shapes within the generally tubular shape are designed to restrain and hold an affected joint in a resting position comfortably so that the splint can be worn for extended periods including throughout the night and easily removed and re-applied without cumbersome attachment methods. In the preferred embodiment for treatment of wrist injuries, a sleeve extending from the fingers to the elbow contains a foam ball sewn into the construction at the location of the wearer's palm and a thumb-hole to position and secure the splint on the wearer's forearm.

10 Claims, 2 Drawing Sheets

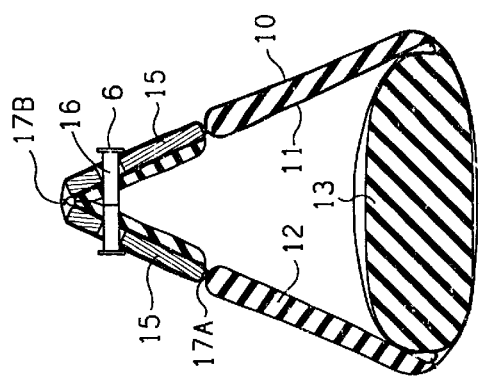
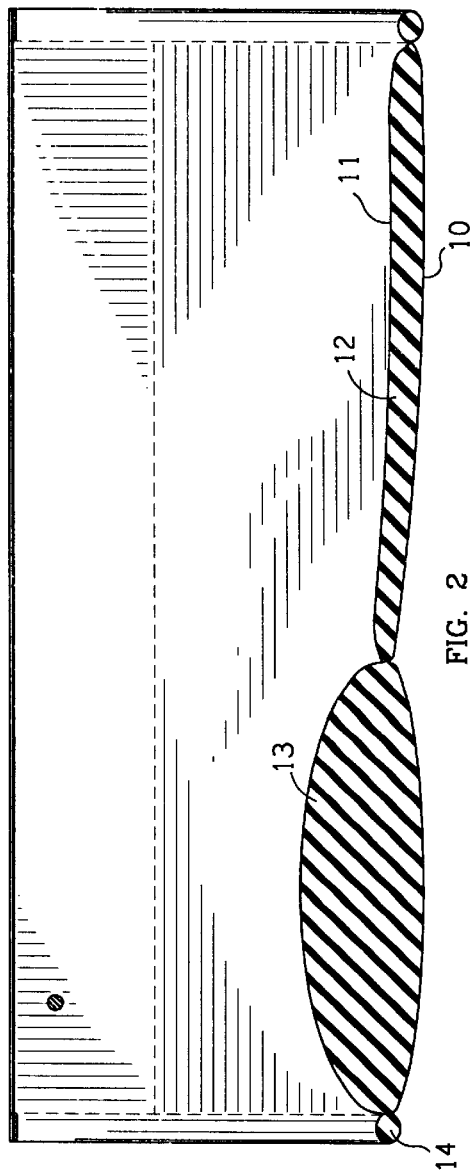
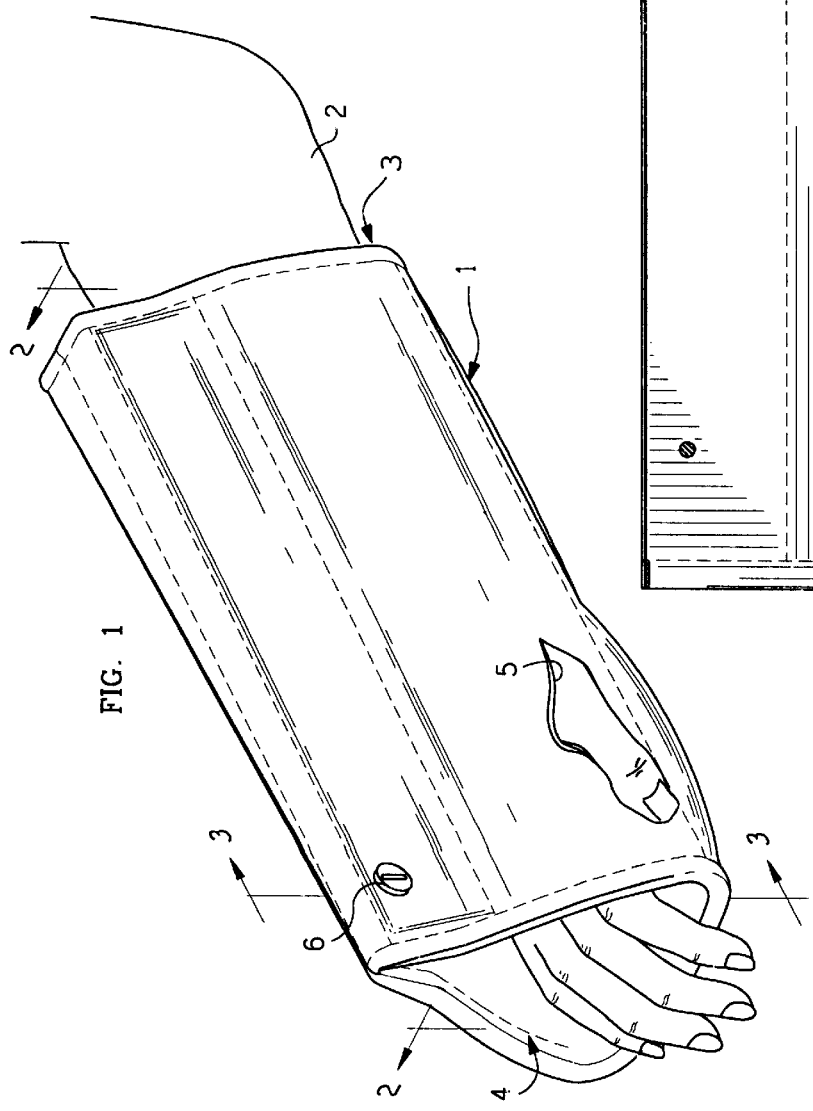

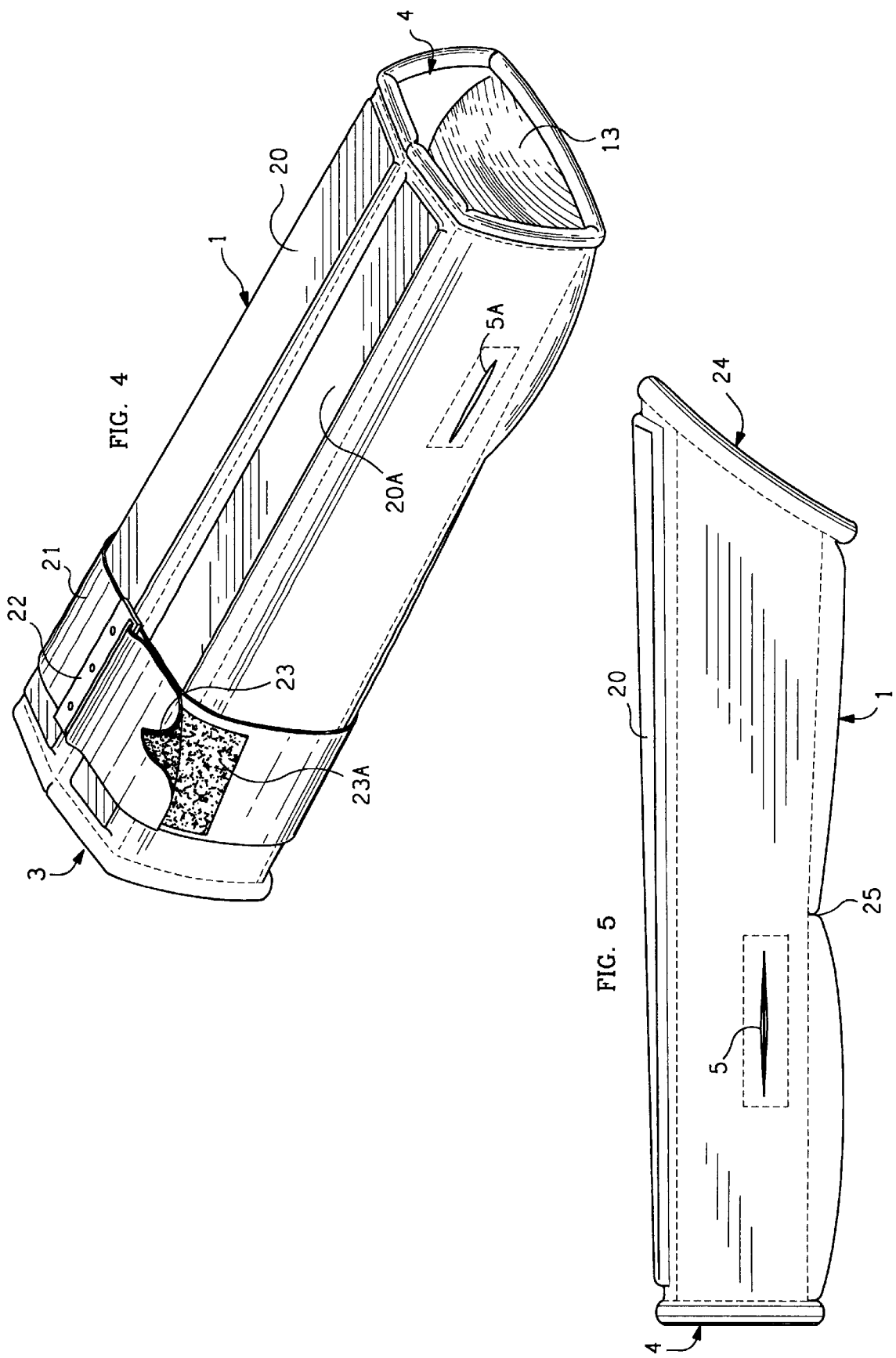

NIGHT SPLINT

BACKGROUND OF THE INVENTION

The field of the within described invention is orthopedic braces and splints for treatment of human medical conditions such as repetitive strain injury and tendonitis. Specifically, the preferred embodiment described is a sleeve of soft material, stiffened by battens and immobilizing the affected joint in a resting position that will enhance recovery.

DESCRIPTION OF THE RELATED ART

Immobilization of body parts by means of plaster casts, braces, splints, or strap and buckle harnesses has long been known and widely utilized. Designs of the various immobilizing devices for various limbs, joints, broken bones, and soft tissue ailments have taken as many forms as there are ailments and sizes and shapes of people. As anthropometric dimensions of various applications vary widely, the customization of such braces is often necessary, the most obvious of these being plaster casts which are specifically molded to the patient in exactly necessary size and shape. Increasingly, newly recognized ailments of arthrology are addressed by constructions that address a single ailment, sometimes in an adjustable and reusable configuration.

Of these ailments that are the subject of new awareness, chief among them may be Carpal Tunnel Syndrome (CTS), a nerve inflammation injury at the point that the nerve passes through and is subject to pressing in the boney passageway through the wrist. CTS is recognized to be remarkably increased among the population of computer keyboard users and misusers as a result of repetitive typing motions, a machine-bites-man dilemma. In fact, CTS is a special case of Repetitive Stress Injury(RSI) which can similarly strike many joints, tendons, ligaments and muscle tissues of the body that are subject to repeated cycles of similar movement over long periods of time. RSI generally and CTS particularly are epidemic, result in tremendous lost working time and productivity, and can be very painful and even completely disabling to the sufferer.

Treatment of RSI can be problematic and nonspecific, as individual symptoms and causative conditions also vary widely. Since subjective reports of pain are the principal diagnostic tool, precise diagnosis is difficult. Worse, since the repetitive motion that caused the injury may of necessity continue during treatment, as in employment-related activities of typing, product assembly, musical instrument play, and machine operations, the treatment may be delayed, compounded or just ineffective. Cumbersome immobilizing devices are typically not compatible with the need to continue the motion, as most restraining braces for instance cannot be worn during the flexible motions required for typing or other repetitive activity.

As RSI is so widespread, there is a corresponding need for treatment and treatment devices that may be efficiently and economically provided to the population. In this regard, the prior art of medical restraining devices for affected injured joints are costly, often complex, often customized, and distributed through a supply system for medical devices that is layered with overhead charges. A simplified, effective, self-administered remedy and appliance for treatment of RSI is urgently required.

A primary treatment for RSI of all types is immobilization of the affected joint for rest and recovery of injured nerves and tissues. For instance the numb fingers that are characteristic of CTS, caused by swollen tissues around the carpal tunnel pressing against nerves can be relieved by resting periods that enable renewal and restoration of normal state of the tissues. As movements such as ulnar deviation, wrist drop, hyperextension of fingers and excessive supination due to poor posture can be prevented by immobilization, periodic rest at night may provide rest and repair for damage caused by motion during the day. Even more clearly, the microscopic tears in tendons, ligaments and muscles that result from many body motions benefit from relaxation as capillaries are opened to maximal blood flow bringing oxygen and nutrients and carrying away waste products. Further ailments such as tenosynovitis, or inflammation of the sheath that surrounds a tendon, and medial epcondylitis, or tiny tears in tissues on the inside of repetitively stressed joints, are relieved by immobilization, the longer and more often the better. Therefore a maximum of comfort and convenience in the treatment method will encourage sufferers to regularly engage in the immobilizing treatment.

Thus it is an object of the within invention to provide a simple, easily administered device for treatment of repetitive strain injury and carpal tunnel syndrome in particular.

Another object of the invention is the design of a joint restraining device that will immobilize the affected joint for maximum relief, rest and recovery for extended periods.

Yet another object of the device described is to accommodate a wide range of anthropometric variation in the same device without need of complex adjustments or multiple sizes.

Another object is to provide a joint immobilizing device that may be re-used without limitation.

Another object is the design of a splint that is sufficiently soft and comfortable that it may be worn during sleep without any discomfort or danger to the user.

Yet another object of the splint is be maximally comfortable in order that pain is reduced as much as possible.

A final object of the invention is to accommodate a variety of applications within the spirit of the preferred embodiment that may address and be designed for treatment of strain to any articulating joint or the surrounding tendons, ligaments or musculature, including feet, ankles knees, elbows and shoulders.

BRIEF SUMMARY OF THE INVENTION

A tube-shaped soft padded material construction is described for application principally at night to immobilize an affected joint. While the preferred embodiment and first application described below is targeted to the wrist and CTS-type symptoms, this application is not to be read as a limitation, as the same design methodology and device could apply to many joints and ailments thereof.

As the longest uninterrupted period of rest available for restraint and recovery of the affected joint is during sleeping hours at night, the splint is designed to be donned easily and worn comfortably to minimize sleep disruption or discomfort, and is therefore illustrated below in a fabric quilting construction. The soft quilting is not only comfortable and warm for night wear, but is also designed to be soft such that moving the affected limb and striking a blow against either the wearer's body or a bed companion's body will soften the blow. Of course, in order to maintain the restraint for which the splint is designed, the soft construction must be stiffened, and a pair of wooden battens in sewn pockets within the quilting is illustrated as a straightforward stiffening means that will not significantly diminish the benefits of the soft construction or overly rigidify the entire construction. A further advantage to the quilted style of construction of the splint is that a range of sizes of the wearer's limb are accomodated by the compressibility of the batting material and expansibility of the fabric; thus the uncompressed, unexpanded soft-sided splint will fit a wearer's limb at the small end of the human size range, yet still expand the fabric and compress the batting as it is fitted to the limb of a wearer at the high end of human range; sampling experiments have shown that one size of soft-sided splint will accomodate well over 90% of the range of human limb sizes without adjustment.

A defining principle of the invention is that the affected joint should be immobilized exactly in the position of rest that will relieve pressure and prevent movement on the affected area, and that the device should conveniently be worn for the longest period of daily time that the user can afford to dedicate to rest and therapy. This recognizes fully that in RSI the immobilization cannot usually be continuous, as work must go on. Therefore the device must also be easily removable and easily resumed without need of multiple fastening operations or even destruction of the device, such as would occur with removal of taping or a cast.

Such a device is also useful in prevention of RSI by resting joints and allowing recovery from repetitive strains even before they accumulate to disable a worker. Providing the device inexpensively to workers to wear at night who are susceptible to RSI by a particular job, motion, or personal inclination would reduce loss of productivity dramatically.

Therapy to the affected joint by enabling and advising the user to wear the soft splint described herein through the evening and night is an effective capture of maximum daily treatment time. Night wear of the appliance as a routine will address not only long-term damage and recovery, but provide as well a daily recovery from ongoing daily strain or even act as a preventive measure.

The specific design application for CTS is a sleeve that extends from approximately just forward of the elbow, extends the forearm, surrounds the wrist, and closely contains the hand, allowing fingers to extend at the end and resting the palm on a padded ball constructed of foam rubber or other resilient comfortable material and contained in a sewn pocket of the fabric sleeve. The entire tubular shape is stiffened by battens and is further stabilized to the correct position by a hole at the thumb position through which the thumb comfortably extends. Thus the hand and wrist are immobilized in a natural, slightly flexed pronated position in which the nerves running through the carpal tunnel are free from contact and restrained from distressing movement. Since many joints subject to this therapeutic approach are both right and left sided, a generally tubular construction may be adapted to use the same unit on either side of the body, with appropriate features on both sides of the unit; for instance, a restraining thumb protrusion opening is provided on the both the right and left side of the arm splint illustrated as the preferred embodiment, such that the same splint can be worn on either right or left arm.

Of course, this strictly non-invasive non-medication modality may be supplemented or used in conjunction with any other treatment modality for CTS without conflict.

BRIEF DESCRIPTION OF THE DRAWINGS

FIG. 1 is a perspective view of the night splint device applied to a user's hand and arm, showing the hand and wrist held in slightly flexed pronated position.

FIG. 2 is a cross section of the night splint along lines 2—2 of FIG. 1 (but for clarity omitting the wearer's hand shown in FIG. 1), showing construction of the soft-sided splint.

FIG. 3 is a cross section of the night splint along lines 3—3 of FIG. 1 (but for clarity omitting the wearer's hand shown in FIG. 1), showing construction of the soft sided splint.

FIG. 4 is a perspective view of a modified application of the invention adapted for treatment of tennis elbow.

FIG. 5 is a side view of yet another modified application of the device both lengthened cutback at one end to partially immobilize the forearm and elbow joint.

DETAILED DESCRIPTION OF THE INVENTION

Turning to FIG. 1 of the drawings it may be seen that the tubular splint (1) in the shape of a vambrace is designed for simple insertion of the user's forearm (2), providing an entry end opening (3) of the tube for insertion and an exit end (4) from which the fingers will comfortably extend in a resting position, and a thumb opening (5). Although not visible here, another thumb opening is provided on the opposite side, in order that the splint may be worn on either the left or right arm, the unit being essentially laterally symmetrical. The entire splint unit is stiffened sufficiently to prevent any significant bending of the unit from end to end by a pair of battens inserted in sewn pockets along the upper ridge of the tube. While the battens will lay approximately flat against the upper portion of the arm, an optional batten screw (6) may further stiffen the splint by drawing the battens together for reinforcement of rigidity and incidentally quickly adjusting the size of the splint by reducing the tubular volume for tighter fit or smaller limb.

FIG. 2 illustrates construction details of the splint in longitudinal cross section, showing the outer fabric shell (10) and inner fabric shell (11) from which the splint is basically constructed, simply and economically. The comfort and sturdiness of the splint is furthered by inclusion of batting (12) which may be cotton or foam rubber or other suitably soft resilient volumetric material which is applied throughout the construction of the splint. Sewn beading (14) is provided as a construction detail to terminate the tube at the openings. At the position of the palm, the lower splint surface enclosed a larger volume of batting or foam as a ball or convex inner surface which fits into the palm gently but effectively restraining the hand from movement. As the upper area of the splint stiffened by the battens will restrain the hand and wrist from upward or supinating movement, so the palm ball restrains the hand from undue downward or pronating movement and side-to-side flexion is restrained by the general longitudinal stiffness of the batten-stiffened tube.

FIG. 3 further illustrates in transverse cross section that the soft-sided construction method is carried around the circumference of the tube as outer fabric shell (10) and inner fabric shell (11) form a batting-containing chamber (12) in sections divided by stitching to form bottom chamber, 2 side chambers and 2 upper chambers which enclose either the batting(12) or foam palm ball (13). The wood battens (15) are also enclosed in the upper chambers formed by stitching at the compression points (17A) and (17B), and run the length of the splint. The screw barrel (16) of batten screw (6) is shown holding the battens in a closed position that can be seen to provide stiffness and sizing of the tube, and it can be seen that with removal of the screw and screw barrel the battens would lie flat, increasing the cross section area of the tube and thus accommodate a somewhat larger arm.

FIG. 4 depicts an alternate embodiment of the soft splint which further includes a forearm strap (21) and a fastening buckle (22) through which the strap end is led and secured back over itself by VELCRO™ loop patch (23) and VELCRO™ hook patch (24). Thus the forearm and its musculature, tendons and ligaments may be tightly restrained from extension as is found to be beneficial as resting therapy for tendonitis or tennis elbow, and at the same time the wrist and hand are comfortably restrained as described in association with FIG. 1.

Also visible in FIG. 4 are the mirror right side thumb hole 5A, provided for left hand wear, as the thumb hole on the left accommodates right hand wear of the same unit. Top batten pockets 20 and 20A are also seen here, the pair of battens lying essentially flat against the top of the wearer's arm in the absence of the optional batten screw described in FIG. 1.

FIG. 5 is another alternate embodiment for application to the forearm and hand showing a modified arm entry opening (24) and clearly showing the bottom stitch point (25) that separates the body of the tube from the chamber containing the palm ball.

Thus in the various views of the preferred embodiment and similar devices for immobilization of the forearm, it can be seen that the wrist and hand of the sufferer of carpal tunnel syndrome are comfortably held in a position of rest, slightly flexed and pronated, that will relieve the stress of motion that cause the injury. While the causes of CTS may vary in individual cases, it is always beneficial to immobilize the joint in a neutral position for extended times to allow recovery.

Examining the drawings and explanation above may also enable the reader to understand that the same device could be adapted for other joints as a soft-sided batten-stiffened restraining night splint. For instance a sleeve construction may be made for insertion of the foot which would restrain flexion, abduction and eversion in the same way that the arm-wrist splint restrains flexion, pronation and supination. While the construction to enclose the foot and ankle would be angled, the basic tubular construction with an entry end and a terminating end described and illustrated for the arm would still otherwise apply. Suitable applications for other joints, such as knees, shoulders and hips embodying the same design and function criteria detailed above would also be efficacious and within the spirit of the invention.

In all of the described and projected applications, the appearance and feel of a comfortable device are important to encourage frequent and extended use. The sleeping period at night is the longest uninterrupted and nonstressing period of the day for most people, and the best suited for immobilizing injured joints that must be used again the next day. The soft-sided night splint with little or no complicated closure devices is easily slipped on at bedtime or during TV time, and easily slipped off in the morning. The soft design is also important during sleep as it will not chafe or injure by impact of a swinging arm either the wearer or a bed companion.

Comfort is emphasized in the construction and function of this invention because relief of pain is an important treatment objective. Pain of RSI can be extreme and disabling to point of forcing inactivity, which rather than being restful, results in weakened muscles, further hampering recovery. Therefore the use of the within described splint as it is easily applied and removed actually encourages both periods of rest and recovery and alternating periods of activity with the splint removed.

Another benefit to a splint specially designed for night wear is that extended wearing will teach the user both consciously and subconsciously, as well as in "muscle memory" to keep the affected joint in a neutral nonstressed position as much as possible, returning it to the position of rest in between repetitive motion. For instance, a CTS sufferer who wears the night splint every night may tend to learn to hold and return the hand to the slightly flexed pronated position of rest that is enforced during his time in the splint, and will learn to rely more on his shoulder muscles in repetitive movements and less on wrist and finger movement, resulting in a long-term reduction of stressing not available in any other treatment method.

I claim:

1. A hand, wrist and forearm splint for minimizing the effects of carpal tunnel syndrome such that the hand and wrist joint of a user may recover from stress injury by periods of therapeutic immobilization, comprising:

a soft-sided construction with an inner fabric shell and an outer fabric shell, said inner and outer shells joined to form a compartment substantially filled with resilient volumetric material, said construction being formed to enclose a generally tubular space corresponding to the shape of the forearm and extended and fitted to closely restrain the wrist, hand, and forearm of a user, said tubular shape having an open entry end and a terminating end, means for stiffening said soft-sided construction longitudinally, said means being positioned in a top portion of said shell, and a semi-spherical ball of resilient material contained within the fabric shell at a position corresponding to the palm during use such that the hand rests on the ball and the wrist is constrained to a neutral resting position.

2. The device of claim 1 wherein the soft-sided construction is comprised of quilting.

3. The device of claim 1 wherein the said resilient volumetric material is batting.

4. The device of claim 1 wherein the said resilient volumetric material is foam rubber.

5. The device of claim 1 wherein said means for stiffening is one or more battens enclosed in compartments within said soft-sided construction.

6. The device of claim 1 further comprising openings at the position of the thumb.

7. The device of claim 1 wherein the terminating end is open such that the fingers may extend from the terminating end yet be restrained in resting position.

8. The device of claim 1 further comprising a circumferential tensioning strap located along the length of said tubular construction to further restrain movement of said jointed body section, and adjustable means for fastening said strap in tensioned position.

9. The device of claim 8 wherein said means for fastening is mating patches of hook-and-loop fastener on said strap.

10. The device of claim 8 wherein said means for fastening is a buckle.

* * * * *